United States Patent
Baba et al.

(10) Patent No.: US 9,278,899 B2
(45) Date of Patent: Mar. 8, 2016

(54) METHOD FOR PRODUCING 3,5-DIMETHYLDODECANOIC ACID; AND 4-CARBOXY-3,5-DIMETHYL-3,5-DODECADIENOIC ACID

(71) Applicant: Shin-Etsu Chemical Co., Ltd., Tokyo (JP)

(72) Inventors: Akihiro Baba, Joetsu (JP); Takeshi Kinsho, Joetsu (JP); Naoki Ishibashi, Joetsu (JP)

(73) Assignee: Shin-Etsu Chemical Co., Ltd. (JP)

( * ) Notice: Subject to any disclaimer, the term of this patent is extended or adjusted under 35 U.S.C. 154(b) by 0 days.

(21) Appl. No.: 14/713,582

(22) Filed: May 15, 2015

(65) Prior Publication Data
US 2015/0344395 A1 Dec. 3, 2015

(30) Foreign Application Priority Data
May 27, 2014 (JP) .................................. 2014-109166

(51) Int. Cl.
| | | |
|---|---|---|
| C07C 51/36 | (2006.01) | |
| C07C 51/373 | (2006.01) | |
| C07C 51/09 | (2006.01) | |
| C07C 51/38 | (2006.01) | |
| C07C 57/13 | (2006.01) | |

(52) U.S. Cl.
CPC ............... *C07C 51/36* (2013.01); *C07C 51/09* (2013.01); *C07C 51/373* (2013.01); *C07C 51/38* (2013.01); *C07C 57/13* (2013.01)

(58) Field of Classification Search
CPC combination set(s) only.
See application file for complete search history.

(56) References Cited

PUBLICATIONS

Rodstein et al. "Identification and Synthesis of a Female-Produced Sex Pheromone for the Cerambycid Beetle *Prionus californicus*", J. Chem. Ecol. 35:590-600 (2009).
Rodstein et al. "Determination of the Relative and Absolute Configurations of the Female-Produced Sex Pheromone of the Cerambycid Beetle *Prionus californicus*", J. Chem. Ecol. 37:114-124 (2011).
Petrow et al. "Synthese and oberflächenaktive Eigenschaften der verzweigten Säuren der Reihe $C_nH_{2n+1}COOH$ der Zusammensetzung $C_{10}$-$C_{20}$", Fette Seifen Anstrichmittel 61:940-946 (1959).
Henrick et al., "Stereoselective Synthesis of Alkyl (2E, 4E)- and (2Z, 4E)-3,7,11-Trimethyl-2,4-dodecadienoates. Insect Growth Regulators with Juvenile Hormone Activity," The Journal of Organic Chemistry, vol. 40, No. 1, Jan. 10, 1975, pp. 1-7.
European Search Report, European Application No. 15168196.2, Oct. 14, 2015, 4 pages.

*Primary Examiner* — Yate K Cutliff
(74) *Attorney, Agent, or Firm* — Myers Bigel Sibley & Sajovec

(57) ABSTRACT

Provided is a process for producing 3,5-dimethyldodecanoic acid, which is an active ingredient of the pheromone of California *prionus*, and 4-carboxy-3,5-dimethyl-3,5-dodecadienoic acid which is an intermediate useful for producing 3,5-dimethyldodecanoic acid. More specifically, provided is a method for producing 3,5-dimethyldodecanoic acid, comprising the steps of subjecting 3-methyl-2-pentene-1,5-diacid diester (1) and 2-nonanone (2) to a condensation reaction and subsequent hydrolysis into 4-carboxy-3,5-dimethyl-3,5-dodecadienoic acid (3); decarboxylating or decarboxylating and hydrolyzing the 4-carboxy-3,5-dimethyl-3,5-dodecadienoic acid (3) into 3,5-dimethyl-2,4-dodecadienoic acid (4); and hydrogenating the 3,5-dimethyl-2,4-dodecadienoic acid (4) into 3,5-dimethyldodecanoic acid (5), as shown in the following scheme:

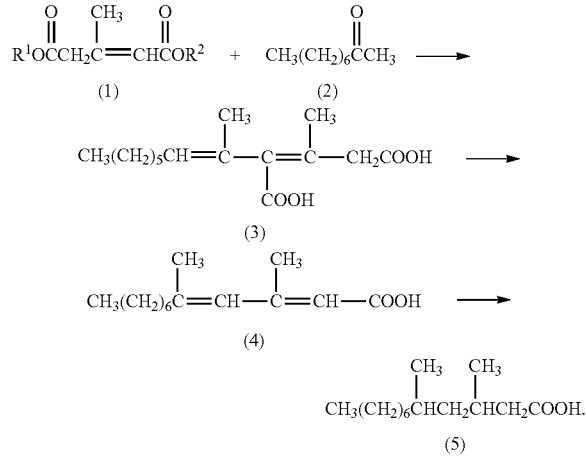

2 Claims, No Drawings

METHOD FOR PRODUCING 3,5-DIMETHYLDODECANOIC ACID; AND 4-CARBOXY-3,5-DIMETHYL-3,5-DODECADIENOIC ACID

RELATED APPLICATION

This application claims priority from Japanese Patent Application No. 2014-109166, filed May 27, 2014, the disclosure of which is incorporated by reference herein in its entirety.

FIELD AND BACKGROUND OF THE INVENTION

The present invention relates to a method for producing 3,5-dimethyldodecanoic acid, which is a sex pheromone of California prionus (Prionus californicus), and relates to 4-carboxy-3,5-dimethyl-3,5-dodecadienoic acid, which is an intermediate of the dimethyldodecanoic acid.

Sex pheromones of insects are usually bioactive substances released by individual females and having a function of attracting individual males. They show high attracting activity even in small amounts. Sex pheromones are widely used as a means for predicting the outbreak of insects or finding geological diffusion thereof (emergence into specific areas) or as a means for pest control. As a means for pest control, control methods called "mass trapping", "lure & kill or attract & kill", "lure & infect or attract & infect", or "mating disruption" have been widely carried out in practice. To utilize a sex pheromone, economical production of a required amount of an active ingredient of the pheromone is necessary for basic research and further for a practical application.

California prionus (Prionus californicus), one of long horn beetles, has a wide distribution in Northwestern America. It is an insect pest to various kinds of perennial plants. Among them, damage by this insect pest to hops has been a serious problem. This insect pest has a life cycle as long as 3 to 5 years but it spends most of its life as a larva in soil, more specifically, in the roots or trunks of plants such as hop to be damaged by the insect pest so that it cannot be controlled easily by agrichemicals.

Millar et al. have revealed that as a result of syntheses of candidate compounds presumed from the mass spectra of an extract from this insect pest, the sex pheromone of the insect pest is 3,5-dimethyldodecanoic acid (J. Chem. Ecol., 2009, 35, 590-600). Also in this journal article, Millar et al. synthesize this product by bromination of 2-methyl-1-nonanol, subsequent conversion into a corresponding Grignard reagent, and then reaction with β-butyrolactone.

Further, Petrov et al. synthesize 3,5-dimethyldodecanoic acid by coupling between heptyl magnesium bromide and 2-chloro-3-pentene, addition of hydrogen bromide, alkylation of ethyl malonate, hydrolysis of the resulting ester, and decarboxylation (Fette, Seifen, Anstrichmittel, 1959, 61, 940-946).

Still further, Millar et al. stereoselectively synthesize a (3R,5S)-form and a (3S,5R)-form of 3,5-dimethyldodecanoic acid by asymmetric 1,4-addition of methyl magnesium bromide to 2-decenoate ester, reduction of the ester, a Wittig reaction, asymmetric 1,4-addition again of methyl magnesium bromide to the unsaturated ester thus obtained, and finally hydrolysis of the ester (J. Chem. Ecol., 2011, 37, 114-124).

SUMMARY OF THE INVENTION

The method described in J. Chem. Ecol., 2009, 35, 590-600 is far from an industrial synthesis method. It is because β-butyrolactone to be used in the reaction is very expensive and not easily available industrially, and 3,5-dimethyldodecanoic acid obtained by this method cannot be purified by distillation so that silica gel flash chromatography is used for separation or purification.

The method described in Fette, Seifen, Anstrichmittel, 1959, 61, 940-946 is also far from an industrial synthesis method. It is because an alkylation yield of ethyl malonate is 32%, which is very low, and addition of hydrogen bromide is carried out under severe conditions requiring hydrogen bromide in gas form.

In the method described in J. Chem. Ecol., 2011, 37, 114-124, the number of steps necessary for synthesis of 3,5-dimethyldodecanoic acid from 2-decenoic acid is even six and the product yields of asymmetric 1,4-addition conducted twice are as low as 53% and 12%, respectively. A yield of another step is also low so that a total yield from 2-decenoic acid is only 1.7%. From a standpoint of use of silica gel flash chromatography for separating or purifying an intermediate in each step, this method is far from an industrial synthesis method. In addition, 3,5-dimethyldodecanoic acid is obtained only as a crude product and this journal article does not include a purification method thereof.

Thus, when the conventional production methods are used, it is considered to be very difficult to industrially produce a sufficient amount of 3,5-dimethyldodecanoic acid because of various reasons such as yield and isolation or purification of an intermediate or the intended product.

With the foregoing in view, the invention has been made. An object of the invention is to provide a short process for simply and efficiently producing 3,5-dimethyldodecanoic acid, which is an active ingredient of the pheromone of California prionus, for supplying an adequate amount of the active ingredient necessary for biological or agricultural active tests, practical application or use; and to provide 4-carboxy-3,5-dimethyl-3,5-dodecadienoic acid, which is an intermediate useful for the production of 3,5-dimethyldodecanoic acid.

In one aspect of the invention, there is provided a method for producing 3,5-dimethyldodecanoic acid, comprising the steps of:

subjecting 3-methyl-2-pentene-1,5-diacid diester (1):

wherein $R^1$ and $R^2$ may be the same or different and each represents a monovalent hydrocarbon group having from 1 to 5 carbon atoms, and 2-nonanone (2):

to a condensation reaction and subsequent hydrolysis to obtain 4-carboxy-3,5-dimethyl-3,5-dodecadienoic acid (3):

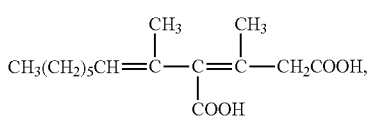

(3)

decarboxylating or decarboxylating and hydrolyzing the 4-carboxy-3,5-dimethyl-3,5-dodecadienoic acid (3) into 3,5-dimethyl-2,4-dodecadienoic acid (4):

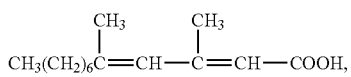

(4)

and hydrogenating the 3,5-dimethyl-2,4-dodecadienoic acid (4) into 3,5-dimethyldodecanoic acid (5):

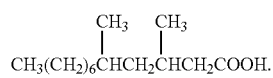

(5)

In another aspect of the invention, there is also provided 4-carboxy-3,5-dimethyl-3,5-dodecadienoic acid represented by the above formula (3), which is an intermediate useful for producing 3,5-dimethyldodecanoic acid.

As will be described later, the product obtained by the step of condensation reaction and hydrolysis may contain the mixture of ten or more unsaturated dicarboxylic acid isomers, and further it may contain lactones obtained by intramolecular cyclization of the unsaturated dicarboxylic acids. Even when the product contains the unsaturated dicarboxylic acid isomer mixture, neither isolation nor purification is necessary because a carbon-carbon double bond portion is reduced into 3,5-dimethyldodecanoic acid, which is a saturated carboxylic acid, in the final hydrogenation step. With regard to the lactone or lactones obtained by intramolecular cyclization of these unsaturated carboxylic acids, reaction of some or all of the unsaturated dicarboxylic acids proceeds through the lactone(s) in the subsequent decarboxylation step so that the lactone(s) contained in the crude product have no influence on the subsequent step. Thus, neither isolation nor purification is required.

On the other hand, the product obtained by the step of decarboxylation or decarboxylation and hydrolysis may contain a mixture of ten or more unsaturated monocarboxylic acid isomers, but the carbon-carbon double bond portion is reduced in the subsequent hydrogenation step into 3,5-dimethyldodecanoic acid, which is a saturated carboxylic acid, so that these isomers contained in the product have no problem.

In the invention, therefore, even in the absence of isolation or purification in the step of condensation reaction and hydrolysis and in the step of decarboxylation or decarboxylation and hydrolysis, purification can be achieved only by distilling the final product obtained by the hydrogenation step.

The invention therefore can provide a production method capable of purifying 3,5-dimethyldodecanoic acid only by distillation of the final product, not requiring purification until the final step. In this method, 3,5-dimethyldodecanoic acid is produced efficiently in the reduced number of steps. In addition, the invention can provide 4-carboxy-3,5-dimethyl-3,5-dodecadienoic acid, which is an intermediate useful for production of 3,5-dimethyldodecanoic acid.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

According to the invention, a starting material is 3-methyl-2-pentene-1,5-diacid diester represented by formula (1) below. In the formula, $R^1$ and $R^2$ may be the same or different and each represents a monovalent hydrocarbon group having from 1 to 5, preferably from 1 to 3 carbon atoms.

(1)

Examples of the monovalent hydrocarbon group represented by $R^1$ and $R^2$ include a linear or branched saturated hydrocarbon group such as methyl, ethyl, n-propyl, n-butyl, n-pentyl and 1-methylethyl; and a linear or branched unsaturated hydrocarbon group such as vinyl, 1-propenyl, 2-propenyl, 2-methyl-1-propenyl, ethynyl, propynyl, and 1-butynyl. A hydrocarbon group having an isomeric relationship with each of them can also be used. One or more hydrogen atoms in the monovalent hydrocarbon group may be replaced by a methyl group, an ethyl group or the like. From these examples of the monovalent hydrocarbon group, an appropriate one can be selected in consideration of reactivity in subsequent reaction or easy availability. For example, when a condensation reaction and hydrolysis described later are carried out to convert the substrate into 4-carboxy-3,5-dimethyl-3,5-dodecadienoic acid (3), each of $R^1$ and $R^2$ is preferably a methyl group, an ethyl group or an n-propyl group because the substrate preferably has a $C_{1-3}$ alkyl group or primary hydrocarbon group which shows high reactivity in hydrolysis.

The 3-methyl-2-pentene-1,5-diacid diester (1) can be synthesized by a known method, for example, the method described in Clive A. Henrick, J. Org. Chem. 1975, 40, 1-7 and the other methods described in the references cited therein.

Next, the step of subjecting 3-methyl-2-pentene-1,5-diacid diester (1) and 2-nonanone (2) to a condensation reaction and then hydrolysis to obtain an unsaturated dicarboxylic acid isomer mixture containing 4-carboxy-3,5-dimethyl-3,5-dodecadienoic acid (3) as shown in the scheme below will be described.

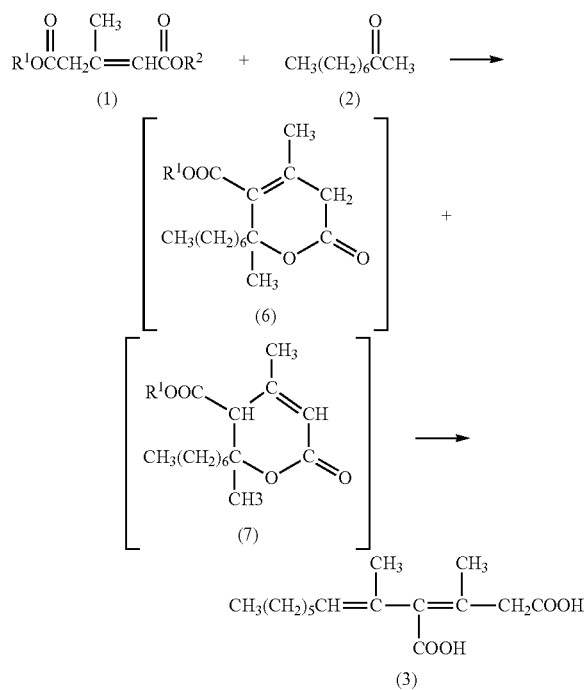

In the condensation reaction between the 3-methyl-2-pentene-1,5-diacid diester (1) and 2-nonanone (2), a portion or all of the substrate is considered to go through a lactone structure as shown in the above formula (6) or (7) during the reaction. The ring opening of these lactones and the hydrolysis reaction of the ester result in the unsaturated dicarboxylic acid isomer mixture containing 4-carboxy-3,5-dimethyl-3,5-dodecadienoic acid (3).

As will be described later, the product obtained by the step of condensation reaction and hydrolysis may contain, in addition to 4-carboxy-3,5-dimethyl-3,5-dodecadienoic acid (3), isomers different in the position of a double bond or geometric isomers thereof. It may further contain lactones obtained by intramolecular cyclization of these unsaturated dicarboxylic acids.

A carbon-carbon double bond portion of the mixture of ten or more unsaturated dicarboxylic acid isomers which may be contained in the crude product is reduced by hydrogenation in the final step into 3,5-dimethyldodecanoic acid, which is a saturated carboxylic acid. Thus, there is no problem even if the products obtained by the step of condensation reaction and hydrolysis contains, in addition to 4-carboxy-3,5-dimethyl-3,5-dodecadienoic acid (3), isomers different in the position of a double bond or geometric isomers thereof. With regard to the lactones obtained by intramolecular cyclization of these unsaturated dicarboxylic acids, a portion or all of the unsaturated dicarboxylic acids go through lactones during the reaction in the subsequent decarboxylation step as described later so that the crude product containing these lactones have no adverse effect in the subsequent step and neither isolation nor purification is required.

Examples of the isomers of the unsaturated dicarboxylic acid and isomers of the intramolecularly cyclized lactones which can be obtained after condensation reaction and hydrolysis are shown below. In addition to Compounds 101 to 114 shown below, there may be, for example, isomers different in the position of a double bond or geometric isomers thereof.

A geometric-isomerism-unspecified compound such as 4-carboxy-3,5-dimethyl-3,5-dodecadienoic acid may be any geometric isomer unless otherwise particularly specified. For example, 4-carboxy-3,5-dimethyl-3,5-dodecadienoic acid may be any of the following compounds 101, 102, 103, and 104 and may be a single isomer or a mixture of two or more isomers.

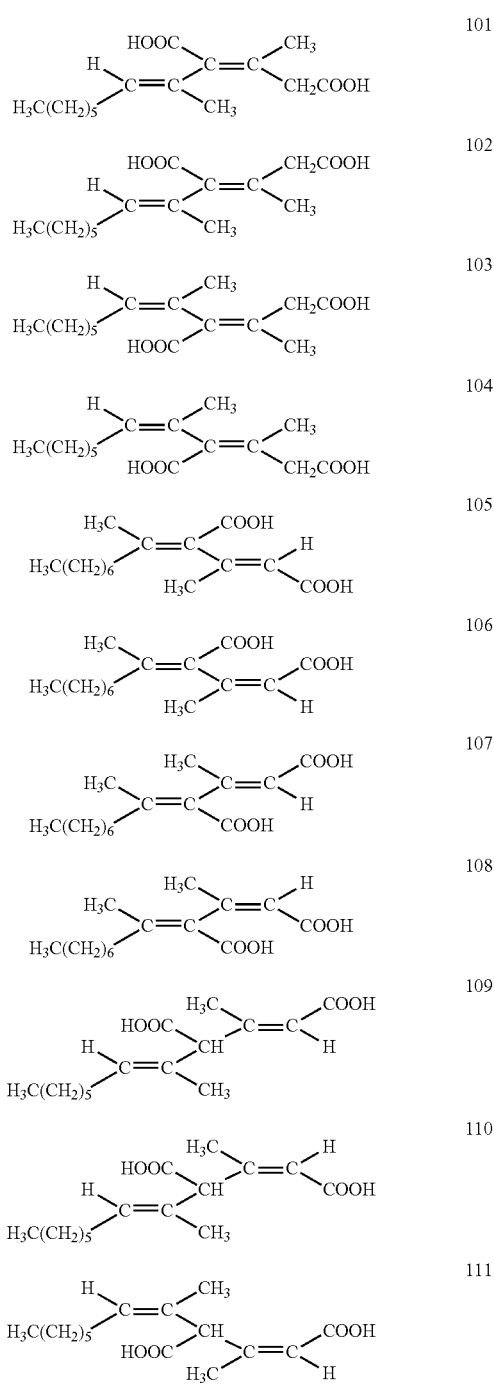

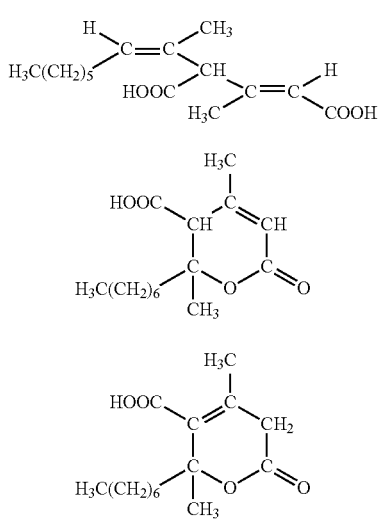

It is preferred to carry out the condensation reaction typically by using from 1 mol to 500 mol of a base per mol of the substrate in the presence of a solvent or in the absence of a solvent, with optional cooling or heating.

Examples of the base to be used in the condensation reaction include alkoxides, preferably alkoxides represented by $R^3OM$ wherein $R^3$ represents an alkyl group, preferably an alkyl group having from 1 to 4 carbon atoms and M represents a metal atom, preferably an alkali metal, such as sodium methoxide, sodium ethoxide, sodium t-butoxide, lithium methoxide, lithium ethoxide, lithium t-butoxide, potassium methoxide, potassium ethoxide and potassium t-butoxide; carbonates such as sodium carbonate, potassium carbonate, sodium hydrogen carbonate and potassium hydrogen carbonate; organic metal reagents such as methyl lithium, ethyl lithium, n-butyl lithium, and methyl magnesium chloride; metal amides such as lithium diisopropylamide, lithium hexamethyldisilazide, sodium hexamethyldisilazide and lithium dicyclohexylamide; hydrogenated metals such as sodium hydride, potassium hydride and calcium hydride; and organic bases such as triethylamine, diisopropylethylamine, tributylamine, N,N-dimethylaniline, N,N-diethylaniline, pyridine, 4-dimethylaminopyridine, pyrrolidine, piperidine, collidine, lutidine, morpholine and piperazine. The base may be used alone or in a mixture of two or more. The base can be selected in consideration of the kind of the substrate, reactivity or selectivity. The base is preferably an alkoxide from a standpoint of reactivity and cost. The alkoxide having from 1 to 3 carbon atoms is particularly preferred because of less steric hindrance. When the alkoxide represented by $R^3OM$ wherein $R^3$ represents an alkyl group, preferably an alkyl group having from 1 to 4 carbon atoms and M represents a metal atom, preferably an alkali metal, is used as the base, $R^1$ and $R^2$ of the substrate may be replaced by $R^3$ by transesterification. Accordingly, the alkoxide having the same group as $R^1$ and $R^2$ of the substrate may be selected in view of preventing the production of complicated products and facilitating evaluation of the condensation reaction. However, an ester of the substrate is converted into the corresponding carboxylic acid in the hydrolysis after the condensation reaction so that even transesterification has no influence on the reaction.

The amount of the base to be used in the condensation reaction differs depending on the kind of the substrate or the base. It is preferably from 1 mol to 100 mol, more preferably from 1 mol to 10 mol per mol of the substrate ester compound.

Examples of the solvent to be used in the condensation reaction include alcohols such as methanol, ethanol, isopropyl alcohol, t-butyl alcohol, benzyl alcohol, methoxyethanol, ethoxyethanol, diethylene glycol monomethyl ether, triethylene glycol monomethyl ether; ethers such as diethyl ether, di-n-butyl ether, tetrahydrofuran and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethylsulfoxide (DMSO) and hexamethylphosphoric triamide (HMPA); and nitriles such as acetonitrile and propionitrile. The solvent may be used alone or as in a mixture of two or more. When the alkoxide $R^3OM$ is selected as the base, the corresponding alcohol ($R^3OH$) is preferably selected.

The amount of the solvent to be used in the condensation reaction is preferably from 0 g to 10000000 g, more preferably from 0 g to 1000 g, relative to one mol of the ester compound as the substrate.

The reaction temperature of the substrate in the condensation reaction is preferably from −78° C. to 200° C., more preferably from −5° C. to 100° C. The reaction time can be selected freely. The reaction time is preferably a period of time for allowing the reaction to proceed sufficiently while monitoring the progress of the reaction by thin-layer chromatography (TLC). The reaction time from 5 minutes to 24 hours is usually preferred.

After the condensation reaction, ring opening of the lactone and hydrolysis of the ester are performed with respect to the substrate. Ring-opening of the lactone and hydrolysis of the ester can be carried out simultaneously by adding an aqueous solution of a hydroxide salt to the reaction mixture obtained by condensation reaction and optionally heating the resulting mixture. Examples of the hydroxide salt include sodium hydroxide, lithium hydroxide, potassium hydroxide and barium hydroxide. The amount of the hydroxide salt is preferably from 0.1 mol to 100 mol, more preferably from 0.1 mol to 10 mol per mol of the ester compound as the substrate. When the hydroxide salt is used as an aqueous solution, it is used preferably at a concentration of from 1 to 50% by weight.

The ring opening of the lactone and hydrolysis of the ester are performed at a reaction temperature of preferably from 20° C. to 100° C. The reaction time can be selected freely. The reaction time is desired from a standpoint of yield to be a period of time for completing the reaction while monitoring the reaction by TLC. The reaction time from about 0.1 to 20 hours is usually preferred.

When the analysis is made by gas chromatography (GC), since a sample is heated at the injection thereof, the unsaturated dicarboxylic acid produced may form a lactone by intramolecular cyclization or may be decarboxylated, which may prevent correct analysis. Monitoring of the reaction only by GC is therefore not preferred.

After completion of the reaction, the crude product can be used as it is in the subsequent step without distillation under reduced pressure or without purification or isolation through a various type of chromatography.

Next, for example, as shown in the scheme below, the unsaturated dicarboxylic acid isomer mixture containing 4-carboxy-3,5-dimethyl-3,5-dodecadienoic acid (3) is decarboxylated into 3,5-dimethyl-2,4-dodecadienoic acid (4), or is decarboxylated into a mixture of unsaturated monocarboxylic acid isomers and lactones obtained by intramolecular cyclization of the unsaturated monocarboxylic acid isomers and then treated under the lactone ring-opening and hydrolysis conditions into 3,5-dimethyl-2,4-dodecadienoic acid (4).

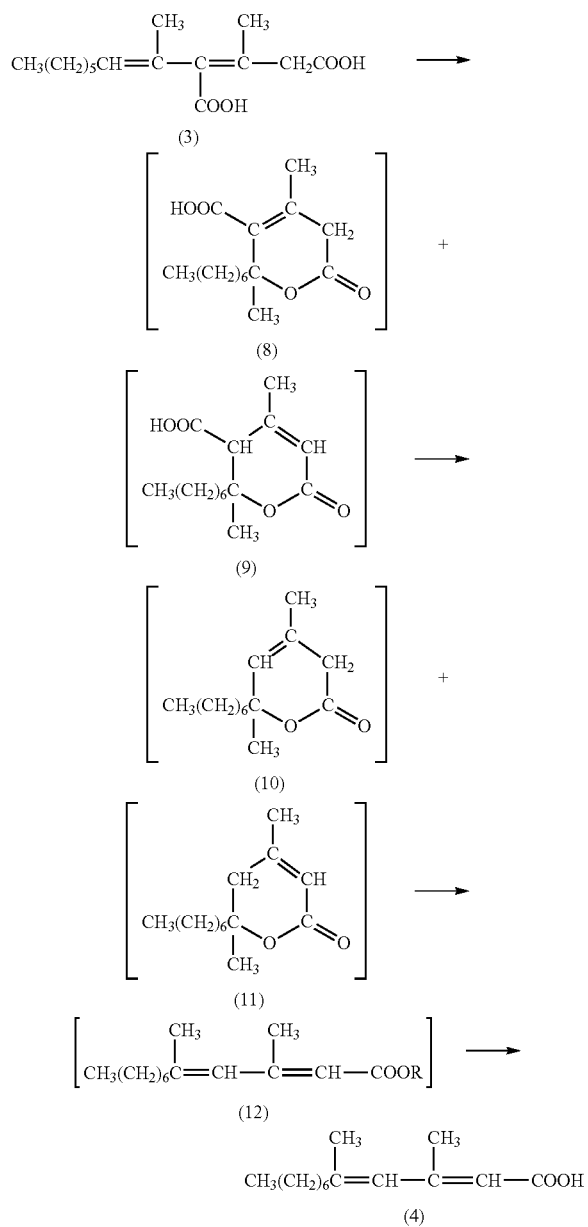

In the decarboxylation reaction of the unsaturated dicarboxylic acid isomer mixture containing 4-carboxy-3,5-dimethyl-3,5-dodecadienoic acid (3), a portion or all of the substrate is considered to become the lactone shown by the above formula (8) or (9) by intramolecular cyclization and then become the lactone shown by the above formula (10) or (11) by decarboxylation. The ring opening of lactone (10) or (11) results in the ester shown by the above formula (12) or the mixture of unsaturated monocarboxylic acid isomers containing 3,5-dimethyl-2,4-dodecadienoic acid shown by the above formula (4). The ester is hydrolyzed into the mixture of unsaturated monocarboxylic acid isomers containing 3,5-dimethyl-2,4-dodecadienoic acid (4). On the other hand, in the decarboxylation reaction of the unsaturated dicarboxylic acid isomer mixture containing 4-carboxy-3,5-dimethyl-3,5-dodecadienoic acid (3), when a portion of the substrate does not become a lactone in the absence of intramolecular cyclization, the unsaturated dicarboxylic acid isomer mixture containing 4-carboxy-3,5-dimethyl-3,5-dodecadienoic acid (3) is directly converted into the unsaturated monocarboxylic acid isomer mixture containing 3,5-dimethyl-2,4-dodecadienoic acid (4).

The decarboxylation reaction is carried out in the presence of a solvent or in the absence of a solvent by using an acid or a base in an amount of preferably from 0.001 mol to 500 mol per mol of the substrate while being optionally heated. Decarboxylation of the substrate occurs only by heating in the presence of a solvent or in the absence of a solvent, but an acid or base is preferably added thereto. Since a base is required for ring opening of the lactone after decarboxylation, a base is particularly preferred.

Examples of the acid to be used in the decarboxylation reaction include mineral acids such as hydrochloric acid, hydrobromic acid, sulfuric acid and nitric acid; organic acids such as acetic acid, oxalic acid, trifluoroacetic acid, methanesulfonic acid, benzenesulfonic acid and p-toluenesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium (IV) methoxide, titanium (IV) ethoxide, titanium (IV) isopropoxide and titanium oxide (IV). The acid may be used alone or in a mixture of two or more.

Examples of the base to be used in the decarboxylation reaction include alkoxides, preferably those represented by $R^3OM$, wherein $R^3$ represents an alkyl group, preferably an alkyl group having from 1 to 4 carbon atoms and M represents a metal atom, preferably an alkali metal, such as sodium methoxide, sodium ethoxide, sodium t-butoxide, lithium methoxide, lithium ethoxide, lithium t-butoxide, potassium methoxide, potassium ethoxide and potassium t-butoxide; hydroxide salts such as sodium hydroxide, lithium hydroxide, potassium hydroxide and barium hydroxide; carbonates such as sodium carbonate, potassium carbonate, sodium hydrogen carbonate and potassium hydrogen carbonate; organic metal reagents such as methyl lithium, ethyl lithium, n-butyl lithium, methyl magnesium chloride and dimsyl sodium; metal amides such as lithium diisopropylamide, lithium hexamethyldisilazide, sodium hexamethyldisilazide and lithium dicyclohexylamide; hydrogenated metals such as sodium hydride, potassium hydride and calcium hydride; and organic bases such as triethylamine, diisopropylethylamine, tributylamine, N,N-dimethylaniline, pyridine, 4-dimethylaminopyridine, pyrrolidine, piperidine, collidine, lutidine, morpholine and piperazine. The base may be used alone or in a mixture of two or more. The base is preferably an organic base from a standpoint of yield. Among the examples of the organic base above, the organic base having a high boiling point such as tributylamine, N,N-dimethylaniline and collidine is particularly preferred for decarboxylation reaction because of allowance of a high-temperature reaction.

The amount of the acid or base to be used in the decarboxylation reaction differs depending on the kind of the substrate or the acid or base. It is preferably from 0.001 mol to 500 mol, more preferably from 0.01 mol to 20 mol, each per mol of the substrate. When the reaction proceeds at a sufficiently fast rate, an amount smaller than a stoichiometric amount is preferably used from a standpoint of cost.

Examples of the solvent to be used in the decarboxylation reaction include water; alcohols such as methanol, ethanol, isopropyl alcohol, t-butyl alcohol, benzyl alcohol, methoxyethanol, ethoxyethanol, diethylene glycol monomethyl ether and triethylene glycol monomethyl ether; ethers such as diethyl ether, di-n-butyl ether, tetrahydrofuran and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethylsulfoxide (DMSO) and hexamethylphosphoric triamide (HMPA); and nitriles such as acetonitrile and propionitrile. The solvent may be used alone or in a mixture of two or more.

The amount of the solvent to be used in the decarboxylation reaction is preferably from 0 g to 10000000 g, more preferably from 0 g to 10000 g, relative to one mol of the ester compound as the substrate.

The reaction temperature in the decarboxylation reaction is preferably from 20° C. to 200° C., more preferably from 140° C. to 180° C. The reaction time can be selected freely. The reaction time is desired from a standpoint of yield to be a period of time for completing the reaction while monitoring the reaction by thin layer chromatography (TLC). The reaction time is usually from about 5 minutes to 96 hours. When the analysis is made by gas chromatography (GC), since a sample is heated at the injection thereof, the unsaturated dicarboxylic acid of the substrate may form a lactone by intramolecular cyclization or may be decarboxylated, and the unsaturated monocarboxylic acid produced by the reaction may also form a lactone by intramolecular cyclization, which may prevent correct analysis. Monitoring of the reaction only by GC is therefore not preferred.

Examples of the compound which may exist as a product after decarboxylation are shown below. In addition to Compounds 201 to 214 shown below, there may be, for example, isomers different in the position of a double bond or geometric isomers thereof.

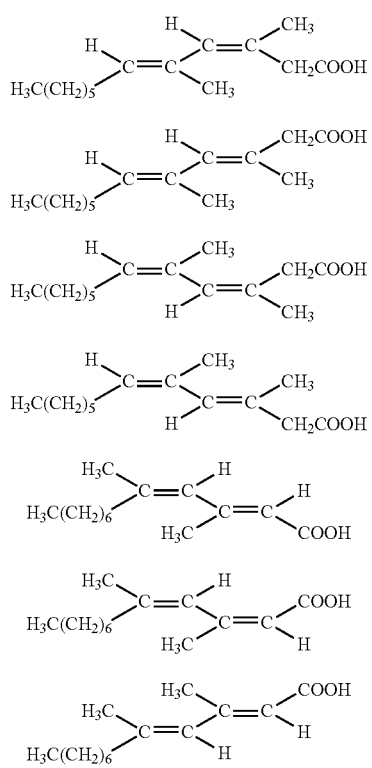

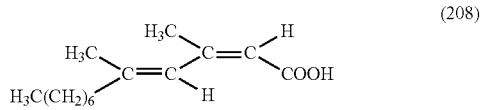

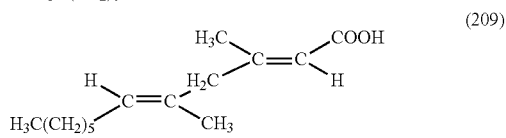

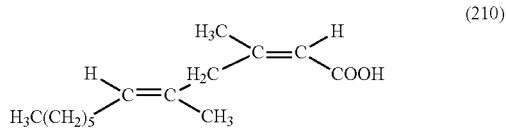

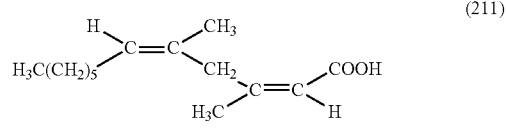

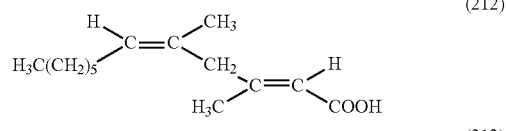

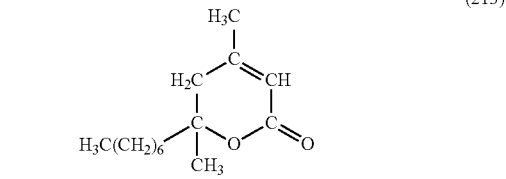

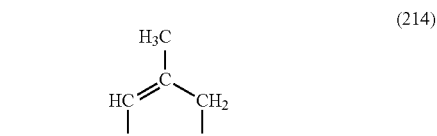

After decarboxylation, a portion or all of the substrate is considered to be present in the form of lactone as shown by the formula (10) or (11) so that a base is added to cause a ring-opening reaction. Examples of the base to be used in the ring-opening reaction include alkoxides, preferably those represented by $R^3OM$, wherein $R^3$ represents an alkyl group, preferably an alkyl group having from 1 to 4 carbon atoms and M represents a metal atom, preferably an alkali metal, such as sodium methoxide, sodium ethoxide, lithium methoxide, lithium ethoxide, potassium methoxide and potassium ethoxide; and hydroxide salts such as sodium hydroxide, lithium hydroxide, potassium hydroxide and barium hydroxide. The base is preferably an alkoxide from a standpoint of reactivity. The alkoxide having from 1 to 3 carbon atoms is particularly preferred because of less steric hindrance.

The amount of the base to be used in the ring-opening reaction differs depending on the kind of the substrate or the base. It is preferably from 1 mol to 500 mol, more preferably from 1 mol to 10 mol, per mol of the lactone of the substrate.

The reaction temperature in the ring-opening reaction is preferably from 20° C. to 200° C., more preferably from 20° C. to 100° C. The reaction time can be selected freely. The reaction time is desired from a standpoint of yield to be a period of time for completing the reaction while monitoring the reaction by TLC. The reaction time is usually from about 5 minutes to 24 hours.

The ester of the above formula (12) obtained after the ring-opening reaction is hydrolyzed into the unsaturated monocarboxylic acid (4). The ester of the substrate is converted into the corresponding carboxylic acid by adding water to the reaction mixture, but addition of an aqueous solution of a hydroxide salt such as sodium hydroxide is particularly preferred from a standpoint of reactivity.

The reaction temperature of the hydrolysis reaction of the ester is preferably from 20° to 100° C. The reaction time can be selected freely. The reaction time is desired from a standpoint of yield to be a period of time for completing the reaction while monitoring the reaction by TLC. The reaction time is usually from about 5 minutes to 24 hours.

Although the crude product after completion of the hydrolysis reaction of the ester is considered to contain, in addition to 3,5-dimethyl-2,4-dodecadienoic acid (4), isomers different in the position of a double bond or geometrical isomers thereof, purification by distillation under reduced pressure or a various chromatography is not required after completion of the reaction and the crude product can be used as it is in the subsequent step.

The crude product may contain a mixture of ten or more unsaturated monocarboxylic acid isomers, but the carbon-carbon double bond portion is reduced into 3,5-dimethyldodecanoic acid, which is a saturated carboxylic acid, in the subsequent step so that there is no problem even if the crude product contains, in addition to 3,5-dimethyl-2,4-dodecadienoic acid (4), isomers different in the position of a double bond or geometrical isomers thereof.

Examples of the unsaturated monocarboxylic acid isomers which may be contained in the crude product are shown below. In addition to Compounds 301 to 312, there may be, for example, isomers different in the position of a double bond or geometrical isomers thereof.

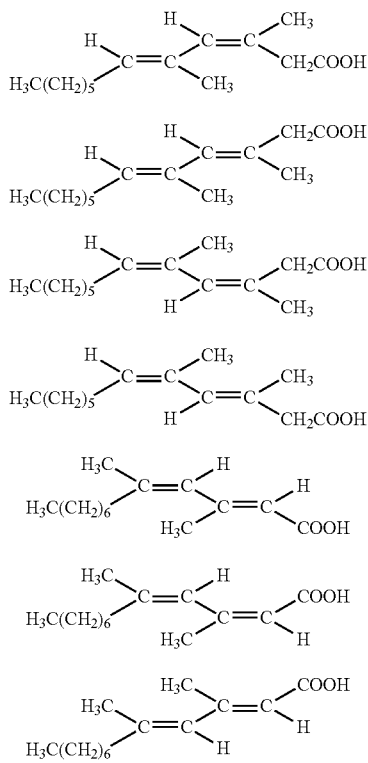

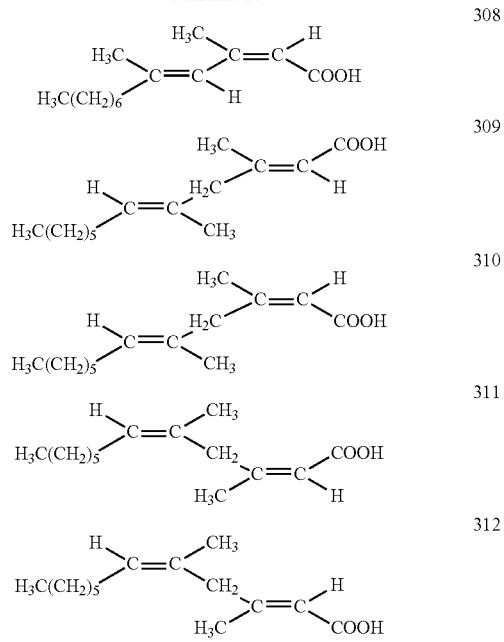

The final step is a hydrogenation step in which intended 3,5-dimethyldodecanoic acid (5) is obtained by hydrogenating the mixture of unsaturated monocarboxylic acid isomers containing 3,5-dimethyl-2,4-dodecadienoic acid (4) as shown in the scheme below.

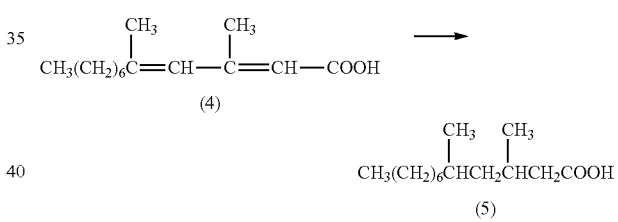

The hydrogenation reaction is carried out usually by using a catalyst in a hydrogen atmosphere, in the presence of a solvent or in the absence of a solvent, in a homogenous system or a heterogeneous system while optionally being cooled or heated.

Examples of the catalyst in the hydrogenation reaction include a metal such as cobalt, nickel, rhodium, palladium, ruthenium, osmium, platinum, iridium, copper, and iron; and an oxide, a hydroxide and a halide, each containing the metal. The catalyst may be used alone or in a mixture of two or more. When the above-mentioned metal catalyst is carried on a carrier, examples of the carrier include carbon, alumina, zeolite and silica gel. Palladium carbon can be given as a particularly preferred example.

Examples of the solvent to be used in the hydrogenation reaction include alcohols such as methanol, ethanol, isopropyl alcohol, t-butyl alcohol, benzyl alcohol, methoxyethanol, ethoxyethanol, diethylene glycol monomethyl ether and triethylene glycol monomethyl ether; ethers such as diethyl ether, di-n-butyl ether, tetrahydrofuran and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethylsulfoxide (DMSO) and hexamethylphosphoric triamide (HMPA); and nitriles such as acetonitrile and propionitrile. The solvent may be used alone or in a mixture of two or more.

The amount of the solvent to be used in the hydrogenation reaction is preferably from 0 g to 10000000 g, more preferably from 0 g to 100000 g, relative to one mol of the ester compound of the substrate.

Hydrogen pressure in the hydrogenation reaction is preferably from normal pressure to 5 MPa, and the reaction temperature is preferably from 5° C. to 70° C., more preferably from 20° C. to 50° C.

The reaction time in the hydrogenation reaction can be selected freely. The reaction time is desired from a standpoint of the yield to be a period of time for completing the reaction while monitoring the reaction by gas chromatography (GC) or thin layer chromatography (TLC). The reaction time is preferably from 5 minutes to 240 hours.

When the analysis is performed using gas chromatography (GC), since a sample is heated at the injection thereof, the unsaturated monocarboxylic acid of the substrate may form a lactone by intramolecular cyclization, which may prevent correct analysis. Therefore, monitoring the reaction only by GC is not preferred.

For isolation or purification of the intended 3,5-dimethyldodecanoic acid, an appropriate method can be selected from purification methods used in the usual organic syntheses, such as distillation under reduced pressure and a various type of chromatography. The distillation under reduced pressure is preferable from a standpoint of industrial economy.

Since isolation or purification is not conducted in the hydrolysis after the condensation reaction and in the hydrolysis after the decarboxylation, ten or more isomers may exist as the unsaturated monocarboxylic acid obtained in the hydrolysis after the decarboxylation. However, the hydrogenation converts them, through reduction of the carbon-carbon double bond portion, into 3,5-dimethyldodecanoic acid which is a saturated carboxylic acid. Thus, isolation or purification is not required in the hydrolysis after the condensation reaction and in the hydrolysis after the decarboxylation. After the step of hydrogenation, purification by distillation under reduced pressure can be carried out.

As described above, a method for simply and efficiently producing 3,5-dimethyldodecanoic acid, which is an active ingredient of pheromone of California *prionus*, can be provided to supply a sufficient amount of the active ingredient of pheromone required for applications or practical use. In addition, 4-carboxy-3,5-dimethyl-3,5-dodecadienoic acid, which is an intermediate useful for the production of 3,5-dimethyldodecanoic acid, can be provided.

Hereafter, specific embodiments of the present invention will be described in detail by way of examples. However, it should not be construed that the present invention is limited to those examples.

EXAMPLES

Synthesis Example 1

Synthesis of 3-methyl-2-pentene-1,5-diacid dimethyl

3-Methyl-2-pentene-1,5-diacid dimethyl which is Compound (1) having $CH_3$ as $R^1$ and $R^2$ will also be described as "Compound (1dMe)".

In a nitrogen atmosphere, 1.04 g of a 28% by weight solution of sodium methoxide in methanol was added dropwise in 5 minutes to a mixture of 9.01 g of methyl 2-oxo-4,6-dimethyl-2H-pyran-5-carboxylate with purity of 99.1% and 8 g of methanol while stirring at room temperature. The purity was based on GC analysis herein and below. The reaction mixture was stirred for one hour under refluxing with heating. After the reaction mixture was concentrated under reduced pressure, distillation under reduced pressure resulted in 5.22 g (91.0% purity) of an intended product A yield calculated from the sum of each fraction weight multiplied by purity thereof with respect to all fractions was 76.5%.

Example 1

Synthesis of unsaturated dicarboxylic acid isomer mixture containing 4-carboxy-3,5-dimethyl-3,5-dodecadienoic acid (3)

(Example in which Sodium Methoxide was Used as a Base)

In a nitrogen atmosphere, 300.39 g of a 28% by weight solution of sodium methoxide in methanol was added dropwise in 40 minutes to a mixture of 89.36 g of 3-methyl-2-pentene-1,5-diacid dimethyl (1dMe) with purity of 90.1%, 82.19 g of 2-nonanone (2) with purity of 98.8% and 90 g of methanol while stirring at room temperature. The reaction mixture was stirred at 65° C. for 3 hours. While stirring the reaction mixture at 65° C., 249.12 g of a 25% by weight aqueous sodium hydroxide solution and 93.42 g of water were added dropwise thereto in 15 minutes. The reaction mixture was stirred for 6 hours at 65° C. The reaction mixture was cooled to room temperature and then extracted twice with 400 ml of n-hexane to separate an aqueous phase from an organic phase. The aqueous phase was subjected to addition of 650 g of 20% by weight hydrochloric acid and then extracted four times with 400 ml of diethyl ether. The work-up including washing, drying and concentration resulted in 135.83 g of an intended crude product. The resulting crude product was used as it was for the next step. The crude product is considered to contain an isomer mixture containing 4-carboxy-3,5-dimethyl-3,5-dodecadienoic acid (3). The physical properties of the crude product are shown below.

Unsaturated dicarboxylic acid isomer mixture containing 4-carboxy-3,5-dimethyl-3,5-dodecadienoic acid (3)

IR (D-ATR): ν=2957, 2927, 2856, 1694, 1644, 1614, 1408, 1378, 1333, 1275, 1250, 1235, 1118, 1060 $cm^{-1}$ $^1$H-NMR (500 MHz, $CDCl_3$): 0.84-0.89 (14.3H, m), 1.17-1.49 (43.6H, m), 1.59 (1.9H, s), 1.65 (0.9H, s), 1.75-1.77 (5.6H, d), 1.83 (1.6H, s), 1.93 (4.1H, s), 1.97 (1.0H, s), 2.01 (1.6H, s), 2.05-2.27 (5.6H, m), 2.30 (2.8H, dd, J=1.6, 4.0 Hz), 2.53-2.56 (1.1H, m), 3.12 (1.4H, s), 3.28 (0.7H, s), 3.33 (0.1H, s), 3.60 (2.9H, s), 3.62 (0.5H, s), 3.78 (0.3H, s), 4.88 (0.3H, s), 5.17-5.19 (0.3H, m), 5.27 (1.6H, dt, J=1.5, 7.3 Hz), 5.31-5.44 (0.6H, m), 5.69 (1.0H, dd, J=1.5, 3.8 Hz), 5.88-5.92 (0.6H, m) ppm.

$^{13}$C-NMR (125 MHz, $CDCl_3$): δ=14.00, 14.04, 15.08, 15.12, 18.34, 20.17, 20.53, 20.64, 20.76, 21.26, 22.57, 23.21, 23.66, 25.06, 27.05, 27.91, 28.89, 28.99, 29.02, 29.06, 29.11, 29.13, 29.40, 29.59, 29.60, 29.62, 29.76, 31.61, 31.63, 31.67, 31.70, 31.75, 35.21, 35.49, 35.52, 37.56, 39.08, 40.45, 40.75, 43.80, 51.56, 51.64, 51.87, 81.76, 86.26, 113.57, 115.80, 118.11, 118.96, 119.39, 119.51, 119.58, 119.74, 129.69, 130.35, 130.49, 131.83, 134.47, 151.30, 155.56, 156.80, 157.95, 158.19, 165.19, 166.54, 170.96, 171.11, 171.27, 171.52, 171.58, 171.66, 171.75, 176.56, 177.38 ppm.

The resulting crude product of (Z,E)-4-carboxy-3,5-dimethyl-3,5-dodecadienoic acid was recrystallized from diethyl ether for the purpose of analyses of physical properties thereof. The results are shown below.

(Z,E)-4-Carboxy-3,5-dimethyl-3,5-dodecadienoic acid (3)

White Crystals
Melting point: 132.4° C.
IR (D-ATR): ν=2957, 2925, 2853, 1712, 1679, 1614, 1424, 1408, 1377, 1335, 1274, 1234, 1189, 1060 cm$^{-1}$.
$^1$H-NMR (500 MHz, DMSO-D$_6$): δ=0.84 (3H, t, J=6.9 Hz), 1.24-1.35 (8H, m), 1.66 (3H, s), 1.76 (3H, s), 2.03 (2H, q, J=7.1 Hz), 3.35-3.39 (2H, m), 5.10 (1H, dt, J=1.5, 7.3 Hz), 12.16 (2H, s) ppm.
$^{13}$C-NMR (125 MHz, DMSO-D$_6$): δ=13.92, 16.58, 21.59, 22.11, 27.37, 28.31, 28.85, 31.15, 39.83, 129.64, 132.29, 135.72, 138.63, 168.71, 171.79 ppm.

Example 2

Synthesis of 3,5-dimethyl-2,4-dodecadienoic acid (4)

(Example in which Decarboxylation was Carried Out Using Tributylamine as a Base)

In a nitrogen atmosphere, a mixture of 15.33 g of an unsaturated dicarboxylic acid isomer mixture containing 4-carboxy-3,5-dimethyl-3,5-dodecadienoic acid (3) and 1.58 g of tributylamine was stirred at 140° C. for 5 hours. The reaction mixture was cooled to 70° C. and 13.20 g of a 28% by weight solution of sodium methoxide in methanol was added dropwise thereto in 5 minutes while stirring at 70° C. The reaction mixture was stirred at 70° C. for 3 hours. While the reaction mixture was stirred at 70° C., 27.36 g of a 25% by weight aqueous sodium hydroxide solution and 30.00 g of water were added dropwise thereto in 5 minutes. The reaction mixture was stirred at 70° C. for 6 hours. The reaction mixture was cooled to room temperature and extracted twice with 20 ml of n-hexane to separate an aqueous phase from an organic phase. The aqueous phase was subjected to addition of 50 g of 20% by weight hydrochloric acid and extracted four times with 100 ml of diethyl ether. The work-up including washing, drying and concentration resulted in 10.93 g of an intended crude product. The crude product thus obtained was provided as it was for the subsequent step. The resulting crude product comprised mainly (Z,E)-3,5-dimethyl-2,4-dodecadienoic acid and (Z,Z)-3,5-dimethyl-2,4-dodecadienoic acid, and was considered to further contain (E,E) and (Z,Z) geometric isomers, isomers different in the position of a double bond, and geometric isomers thereof. The physical properties of the crude product are shown below.

Unsaturated monocarboxylic acid isomer mixture containing 3,5-dimethyl-2,4-dodecadienoic acid (4)

IR (D-ATR): ν=2956, 2927, 2856, 1688, 1626, 1592, 1442, 1378, 1256, 1203 cm$^{-1}$.
$^1$H-NMR (500 MHz, CDCl$_3$): δ=0.84-0.90 (5.9H, m), 1.10-1.48 (19.5H, m), 1.73 (1.5H, d), 1.78 (0.1H, s), 1.82 (1.2H, d), 1.85-1.87 (0.3H, m), 2.03-2.05 (2.9H, m), 2.05-2.13 (2.1H, m), 2.14-2.17 (0.2H, m), 3.05 (0.2H, s), 3.08 (0.1H, s), 4.77-5.64 (0.5H, m), 5.64-5.69 (1.1H, m), 5.76-5.77 (0.1H, d), 6.36 (0.4H, s), 6.41 (0.6H, s) ppm.
$^{13}$C-NMR (125 MHz, CDCl$_3$): δ=14.08, 15.18, 15.50, 16.67, 16.74, 17.80, 18.62, 21.44, 22.49, 22.59, 22.63, 22.66, 23.80, 24.27, 25.66, 25.76, 27.80, 27.96, 29.16, 29.17, 29.64, 31.57, 31.73, 31.80, 33.72, 40.88, 42.08, 42.84, 43.81, 44.53, 44.74, 45.45, 45.71, 65.84, 113,59, 115.67, 116.66, 116.82, 118.98, 123.39, 123.83, 124.64, 127.28, 127.58, 127.75, 128.80, 129.23, 129.29, 129.73, 130.69, 130.72, 131.10, 131.88, 132.12, 132.33, 132.75, 133.66, 142.96, 143.47, 145.68, 147.81, 149.81, 156.25, 156.35, 171.23, 171.30, 171.76, 172.84, 173.59, 178.27 ppm.

Example 3

Synthesis of 3,5-dimethyl-2,4-dodecadienoic acid (4)

(Example in which Decarboxylation was Carried Out Using 2,4-Lutidine as a Base)

In nitrogen atmosphere, a mixture of 1.11 g of an unsaturated dicarboxylic acid isomer mixture containing 4-carboxy-3,5-dimethyl-3,5-dodecadienoic acid (3), 1.32 g of 2,4-lutidine, and 10 ml of toluene was stirred at 100° C. for 5 hours. While the reaction mixture was stirred at 100° C., 1.32 g of 2,4-lutidine was added thereto. The resulting mixture was stirred at 100° C. for 3 hours. The reaction mixture was cooled to 70° C. While the reaction mixture was stirred at 70° C., 0.95 g of a 28% by weight solution of sodium methoxide in methanol was added dropwise thereto in one minute. The reaction mixture was stirred at 70° C. for 3 hours. The reaction mixture was cooled to room temperature, and then 5 g of a 25% by weight aqueous sodium hydroxide solution and 5 g of water were added thereto. The resulting mixture was stirred for 6 hours at room temperature. The reaction mixture was cooled to room temperature, and separated into an aqueous phase and an organic phase. The aqueous phase was subjected to addition of 10 g of 20% by weight, and extracted twice with 10 ml of diethyl ether. The work-up including washing, drying and concentration resulted in 0.89 g of an intended crude product. The crude product thus obtained was provided for the subsequent step as it was.

Example 4

Synthesis of 3,5-dimethyl-2,4-dodecadienoic acid (4)

(Example in which Decarboxylation was Carried Out Only by Heating in the Absence of a Solvent)

In a nitrogen atmosphere, 0.72 g of an unsaturated dicarboxylic acid isomer mixture containing 4-carboxy-3,5-dimethyl-3,5-dodecadienoic acid (3) was stirred at 140° C. for 5 hours. While the reaction mixture was stirred at 70° C., 0.63 g of a 28% by weight solution of sodium methoxide in methanol solution was added dropwise thereto in one minute. The reaction mixture was stirred at 70° C. for 3 hours. While the reaction mixture was stirred at 70° C., 1.30 g of a 25% by weight aqueous sodium hydroxide solution and 5.00 g of water were added dropwise thereto in 3 minutes. The reaction mixture was stirred at 70° C. for 6 hours. The reaction mixture was cooled to room temperature, and extracted twice with 10 ml of n-hexane to separate an aqueous phase from an organic phase. The aqueous phase was subjected to addition of 7 g of 20% by weight hydrochloric acid and extracted four times with 5 ml of diethyl ether. The work-up including washing, drying and concentration resulted in 0.50 g of an intended crude product. The reaction was monitored by TLC, revealing that many byproducts having unknown structures were formed during the decarboxylation reaction. It is considered on basis of this result that decarboxylation reaction is preferably carried out in the presence of an acid or a base.

Example 5

Synthesis of 3,5-dimethyl-2,4-dodecadienoic acid (4)

(Example in which Decarboxylation was Carried Out Using an Acid (Sulfuric Acid))

In a nitrogen atmosphere, a mixture of 1.01 g of an unsaturated dicarboxylic acid isomer mixture containing 4-carboxy-3,5-dimethyl-3,5-dodecadienoic acid (3), 0.05 g of concentrated sulfuric acid, and 3 ml of acetic acid was stirred for 5 hours under refluxing with heating. The reaction mixture was ice-cooled and 10 g of a 25% by weight aqueous sodium hydroxide solution was added dropwise thereto. The reaction mixture was stirred at room temperature for one hour. While the reaction mixture was stirred at room temperature, 12 g of 20% hydrochloric acid was added dropwise thereto. The reaction mixture was stirred for 15 minutes and then extracted four times with 5 ml of diethyl ether. The work-up including washing, drying and concentration resulted in 1.54 g of a crude product. While a mixture of 1.54 g of the resulting crude product and 2 ml of methanol was stirred at 70° C., 0.95 g of a 28% by weight solution of sodium methoxide in methanol was added dropwise thereto in one minute. The reaction mixture was stirred at 70° C. for 3 hours. While the reaction mixture was stirred at 70° C., 5 g of a 25% by weight aqueous sodium hydroxide solution and 5 g of water were added dropwise thereto in one minute. The reaction mixture was stirred at 70° C. for 3 hours. The reaction mixture was cooled to room temperature, and extracted twice with 5 ml of n-hexane to separate an aqueous phase from an organic phase. The aqueous phase was subjected to addition of 6 g of 20% by weight hydrochloric acid, and extracted four times with 5 ml of diethyl ether. The work-up including washing, drying and concentration resulted in 1.20 g of an intended crude product. A decarboxylation reaction using a base is considered to be efficient and preferable because the reaction mixture has to be changed from acidic to basic conditions in order to ring-open the substrate which is presumed to be a lactone as a result of decarboxylation.

Example 6

Synthesis of 3,5-dimethyldodecanoic acid (5)

An autoclave having an internal volume of 500 ml and made of a stainless steel was charged with 10.18 g of an unsaturated monocarboxylic acid isomer mixture containing 3,5-dimethyl-2,4-dodecadienoic acid (4), 1.2 g of 10% by weight palladium carbon, and 100 g of ethanol. Hydrogen was added at 0.5 MPa at room temperature thereto and the resulting mixture was stirred for 2 hours. The reaction mixture was subjected to the work-up including filtration and concentration to obtain 10.01 g of an intended crude product. The resulting crude product was purified by distillation under reduced pressure to obtain 5.35 g having purity of 85.16%.

When sodium methoxide was used as a base in the condensation reaction and tributylamine was used as a base in the decarboxylation, the total yield calculated from the sum of each fraction weight multiplied by purity thereof with respect to all fractions was 44.9% as converted from the charge amount of the raw material 3-methyl-2-pentene-1,5-diacid dimethyl. Similarly, when sodium methoxide was used as a base in the condensation reaction and 2,4-lutidine was used as a base in the decarboxylation, the total yield as converted from the charge amount of the raw material 3-methyl-2-pentene-1,5-diacid dimethyl was 21.6%. It is considered on basis of this result that the decarboxylation reaction is carried out preferably at high temperature and a base having a high boiling point is preferably used.

3,5-Dimethyldodecanoic acid (5)

IR (D-ATR): ν=2958, 2925, 2854, 1708, 1463, 1411, 1380, 1295 cm$^{-1}$.

$^{1}$H-NMR (500 MHz, CDCl$_{3}$): δ=0.84-0.89 (6H, m), 0.92-0.97 (3H, m), 1.00-1.17 (2H, m), 1.23-1.34 (12H, m), 1.43-1.50 (1H, m), 2.03-2.18 (2H, m), 2.28-2.40 (1H, m) ppm.

$^{13}$C-NMR (125 MHz, CDCl$_{3}$): δ=14.10, 19.27, 19.37, 20.02, 20.29, 22.68, 26.82, 27.00, 27.63, 27.68, 29.37, 29.91, 29.93, 30.00, 31.90, 36.62, 37.68, 41.47, 42.40, 44.30, 44.55, 179.87, 180.00 ppm.

GC conditions: Column: DB-WAX (product of J&W Scientific) 30 m×0.25 mmφ, Temp: increased from 100° C. to a maximum of 230° C. by 10° C./min, Injection temperature: 230° C., Carrier: He 1 ml/min, Split ratio: 100:1, Detector: FID, retention time: 13.812 min (syn-form) and 13.925 min (anti-form).

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method for producing 3,5-dimethyldodecanoic acid, comprising the steps of:

subjecting 3-methyl-2-pentene-1,5-diacid diester (1):

wherein R$^{1}$ and R$^{2}$ may be the same or different and each represents a monovalent hydrocarbon group having from 1 to 5 carbon atoms, and 2-nonanone (2):

to a condensation reaction and subsequent hydrolysis to obtain 4-carboxy-3,5-dimethyl-3,5-dodecadienoic acid (3):

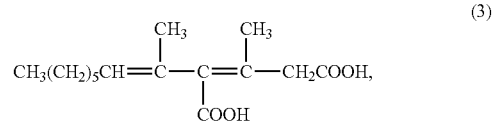

decarboxylating or decarboxylating and hydrolyzing the 4-carboxy-3,5-dimethyl-3,5-dodecadienoic acid (3) into 3,5-dimethyl-2,4-dodecadienoic acid (4):

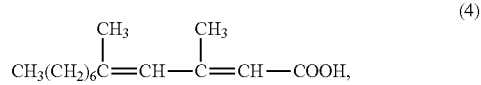

and hydrogenating the 3,5-dimethyl-2,4-dodecadienoic acid (4) into 3,5-dimethyldodecanoic acid (5):

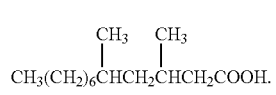 (5)
2. 4-Carboxy-3,5-dimethyl-3,5-dodecadienoic acid represented by the following formula (3):
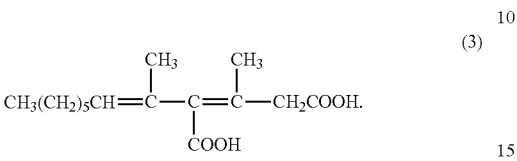 (3)